United States Patent
Duboux et al.

(10) Patent No.: US 11,590,181 B2
(45) Date of Patent: Feb. 28, 2023

(54) SERPIN PRODUCTION

(71) Applicant: SOCIETE DES PRODUITS NESTLE S.A., Vevey (CH)

(72) Inventors: Stephane Duboux, St-Prex (CH); Gabriela Bergonzelli Degonda, Bussigny (CH); Annick Mercenier, Bussigny (CH); Muzi Tangyu, Xi'an (CN)

(73) Assignee: Societe des Produits Nestle S.A., Vevey (CH)

( * ) Notice: Subject to any disclaimer, the term of this patent is extended or adjusted under 35 U.S.C. 154(b) by 117 days.

(21) Appl. No.: 16/958,803

(22) PCT Filed: Dec. 27, 2018

(86) PCT No.: PCT/EP2018/097023
§ 371 (c)(1),
(2) Date: Jun. 29, 2020

(87) PCT Pub. No.: WO2019/129808
PCT Pub. Date: Jul. 4, 2019

(65) Prior Publication Data
US 2021/0060097 A1   Mar. 4, 2021

(30) Foreign Application Priority Data
Dec. 29, 2017   (EP) .................................. 17211072

(51) Int. Cl.
*A61K 35/745*   (2015.01)
*C12N 1/20*   (2006.01)

(52) U.S. Cl.
CPC .............. *A61K 35/745* (2013.01); *C12N 1/20* (2013.01); *C12N 2500/34* (2013.01)

(58) Field of Classification Search
None
See application file for complete search history.

(56) References Cited

U.S. PATENT DOCUMENTS

| | | | |
|---|---|---|---|
| 9,439,449 B2 * | 9/2016 | Holvoet | A23L 33/40 |
| 10,820,616 B2 * | 11/2020 | Destaillats | A23L 33/125 |
| 2011/0177034 A1 | 7/2011 | Kildsgaard et al. | |

FOREIGN PATENT DOCUMENTS

| | | |
|---|---|---|
| EP | 2308498 | 4/2011 |
| JP | 2011507540 A | 3/2011 |
| WO | 2007093619 | 8/2007 |
| WO | 2015085555 | 6/2015 |
| WO | 2017001590 | 1/2017 |

OTHER PUBLICATIONS

Parche et al. J Mol Micrbiol Biotecnol 2007, 12, pp. 9-19.*
Schell et al. "The genome sequence of Bifidobacterium longum reflects its adaptation to the human gastrointestinal tract" PNAS, 2002, vol. 99, No. 22, pp. 14422-14427.
Ivanov et al. "A Serpin from the Gut Bacterium Bifidobacterium longum Inhibits Eukaryotic Elastase-like Serine Proteases" Journal of Biological Chemistry, 2006, vol. 281, No. 25, pp. 17246-17252.
Reimann et al. "Development of a rapid screening protocol for selection of strains resistant to spray drying and storage in dry powder" Beneficial Microbes, 2010, vol. 1, No. 2, pp. 165-174.
Kullin et al. "A functional analysis of the Bifidobacterium longum cscA and scrP genes in sucrose utilization" Appl Microbiol Biotechnoi, 2006, vol. 72, pp. 975-981.
Liu et al. "Proteomics analysis of Bifidobacterium longum NCC2705 growing on glucose, fructose, mannose, xylose, ribose, and galactose" Proteomics, 2011, vol. 11, pp. 2628-2638.
Nissen et al. "Cloning and detection of serpin-like protein encoding gene in Bifidobacterium longum strains" Annals of Microbiology, 2008, vol. 58, No. 1, pp. 127-131.
McCarville et al. "A Commensal Bifidobacterium longum Strain Prevents Gluten-Related Immunopathology in Mice through Expression of a Serine Protease Inhibitor" Applied and Environmental Microbiology, 2017, vol. 83, issue 19, e01323, pp. 1-13.
Parche et al. "Lactose-over-Glucose Preference in Bifidobacterium longum NCC2705: gicP, Encoding a Glucose Transporter, is Subject to Lactose Repression" Journal of Bacteriology, 2006, vol. 188, No. 4, pp. 1260-1265.
Wei et al. "Fructose Uptake in Bifidobacterium longum NCC2705 is Mediated by an ATOP-binding Cassette Transporter" Journal of Biological Chemistry, 2012, vol. 287, No. 1, pp. 357-367.
He Xiang et al. "Proteomic analysis of Bifidobacteria longum strain NCC2705 grown on lactose and glucose" Weishengwu Xuebao—Acta Microbiologica Sinica, 2008, vol. 48, No. 11, pp. 1451-1458.
Dong J. et al. "The Novel Role of a Serpin-Producing Probiotic in Gluten-Related Disorders" Gastroenterology, Apr. 22, 2017, XP085106565.
Yuan et al., "A Proteome Reference Map and Proteomic Analysis of Bifidobacterium longum NCC2705", Molecular and Cellular Proteomics, vol. 5, Issue No. 6, Mar. 20, 2006, pp. 1105-1118.
Japanese Office Action for Appl No. 2020-535090 dated Oct. 4, 2022.

* cited by examiner

*Primary Examiner* — Vera Afremova
(74) *Attorney, Agent, or Firm* — K&L Gates LLP

(57) ABSTRACT

Use of a sugar selected from lactose, fructose and raffinose, for increasing serpin expression in *Bifidobacterium longum* strain CNCM I-2618.

15 Claims, 2 Drawing Sheets

Specification includes a Sequence Listing.

SEQUENCE LISTING

<160> NUMBER OF SEQ ID NOS: 4

<210> SEQ ID NO 1
<211> LENGTH: 20
<212> TYPE: DNA
<213> ORGANISM: Bifidobacterium longum
<220> FEATURE:
<223> OTHER INFORMATION: Primer serpin forward

<400> SEQUENCE: 1
accaatcgct gctaagttcg            20

<210> SEQ ID NO 2
<211> LENGTH: 20
<212> TYPE: DNA
<213> ORGANISM: Bifidobacterium longum
<220> FEATURE:
<223> OTHER INFORMATION: Primer serpin reverse

<400> SEQUENCE: 2
tcgctggcaa gagagtagtc            20

<210> SEQ ID NO 3
<211> LENGTH: 20
<212> TYPE: DNA
<213> ORGANISM: Bifidobacterium longum
<220> FEATURE:
<223> OTHER INFORMATION: Primer ldh forward

<400> SEQUENCE: 3
cgaacgccat ctacatgctc            20

<210> SEQ ID NO 4
<211> LENGTH: 20
<212> TYPE: DNA
<213> ORGANISM: Bifidobacterium longum
<220> FEATURE:
<223> OTHER INFORMATION: Primer ldh reverse

<400> SEQUENCE: 4
aagatctggt tctcttgcag            20

SERPIN PRODUCTION

CROSS REFERENCE TO RELATED APPLICATIONS

The present application is a National Stage of International Application No. PCT/EP2018/097023, filed on Dec. 27, 2018, which claims priority to European Patent Application No. 17211072.8, filed on Dec. 29, 2017, the entire contents of which are being incorporated herein by reference.

FIELD OF THE INVENTION

The present invention relates to bacteria expressing serpin, methods for increasing serpin production in bacteria and uses thereof.

BACKGROUND TO THE INVENTION

Gluten-related disorders comprise all diseases triggered by gluten. They include, amongst other pathophysiology, celiac disease and non-celiac gluten sensitivity. Currently, the incidence of a wide spectrum of gluten-related disorders is growing all around the world, especially for celiac disease and non-celiac gluten sensitivity. Both diseases are triggered by ingestion of gluten. Both innate and adaptive immunity are implicated in celiac disease while innate immunity is implicated in non-celiac gluten sensitivity.

A life-long gluten-free diet is the gold standard treatment for celiac disease and non-celiac gluten sensitivity patients, although it may have some limitations on the extraintestinal manifestations of the disease (Sedghizadeh et al., 2002, Oral Surgery, Oral Medicine, Oral Pathology, Oral Radiology, and Endodontology, 94(4), 474-478). It has been shown that following a strict gluten free diet is very difficult as low level cross-contaminations are difficult to avoid and may happen through the whole food production chain, from grains growth to manufacturing processing (Mitchison et al., 1991, Gut, 32(3), 260-265). Furthermore, it has been described that up to 3 g of hidden gluten might be consumed daily under a strict gluten free diet (Aziz et al., 2014, The American journal of gastroenterology, 109(9), 1498).

Celiac disease is prevalent especially in the United States and Europe where around 1% of subjects had positive antibody tests (Dubé et al., 2005, Gastroenterology, 128(4), S57-S67). It is a complex disorder which arises from a complicated interaction among various immunologic, genetic, and environmental factors (Alaedini & Green, 2005). It is triggered by the digestion of wheat gluten and other related cereal proteins such as rye and barley proteins. Symptoms linked with celiac disease are growth retardation, irritability and pubertal delay in children and many gastrointestinal symptoms such as discomfort, diarrhoea, occult stool, steatorrhea and flatulence, (Dubé et al., 2005; Sedghizadeh et al., 2002).

Non-celiac gluten sensitivity (also named non-celiac wheat sensitivity) is an emerging condition. It is defined as a clinical entity induced by the ingestion of gluten leading to intestinal and/or extraintestinal symptoms which could be improved by removing the gluten-containing foodstuff from the diet (Lundin & Alaedini, 2012). In addition to gliadin (the main cytotoxic antigen of gluten), other proteins/peptides present in gluten and gluten-containing cereals (wheat, rye, barley, and their derivatives) may play a role in the development of symptoms. Non-celiac gluten sensitivity is the most common syndrome of gluten-related disorders with prevalence rates between 0.5-13% in the general population (on average 5%) (Catassi et al., 2013, Nutrients, 5(10), 3839-3853).

Serine protease inhibitors (serpin) are a superfamily of proteins found in eukaryotes (Gettins, 2002, Chemical reviews, 102(12), 4751-4804) and prokaryotes (Kantyka et al., Biochimie, 92(11), 1644-1656).

Recently, human serine protease inhibitors have been shown to play an important role in gluten-related disorders. Elafin is human serine protease inhibitor which shows potent inhibitory capacity against various forms of elastases and proteinase (Ying & Simon, 1993, Biochemistry, 32(7), 1866-1874). Elafin is expressed throughout the epithelium of the gastrointestinal tract and its expression and induction is decreased in patients with inflammatory bowel disease and celiac disease (Baranger, Zani, Labas, Dallet-Choisy, & Moreau, 2011; Motta et al., 2012). Recently, elafin has been identified as a substrate for the cross-linking activity of transglutaminase 2 (TG2) (Baranger et al., 2011, PloS one, 6(6), e20976; Motta et al., Science translational medicine, 4(158), 158ra144-158ra144). In-vitro data shows that the addition of elafin moderately inhibits transglutaminase 2 (TG2) thus inhibiting the deamidation of the digestion-resistant 33-mer gliadin peptide, which is one of the potential triggers of the adaptive immune response in celiac disease (McCarville et al. 2015, Current opinion in pharmacology, 25, 7-12).

Delivery of elafin, produced by a recombinant *Lactococcus lactis* has been shown to reduce gluten-induced pathology and normalise intestine inflammation in a mouse model of gluten sensitivity (Galipeau et al., 2014, The American journal of gastroenterology, 109(5), 748-756). However, this proposed therapy is based on a genetically modified microorganism (GMO) and is therefore not compatible with a food application, as consumer acceptance of GMO is very low.

More recently, serpins have been reported in prokaryotes. In silico analysis revealed the presence of genes encoding serpin-like proteins in different *Bifidobacterium* species. The protein encoded by *B. longum* subsp *longum* (named *B. longum*) NCC 2705 displayed similar antiprotease activity to those of human serpin (Ivanov et al 2006, Journal of Biological Chemistry, 281(25), 17246-17252). *B. longum* NCC 2705 was deposited with the Institute Pasteur, CNCM Collection nationale de cultures de microorganisms, 25, rue du Dr Roux, 75724 Paris Cédex 15, France, according to the Budapest Treaty on 29 Jan. 2001 receiving the deposit no. CNCM I-2618.

It has recently been shown that *B. longum* NCC 2705 (CNCM I-2618), through its serpin production can improve gluten induced pathophysiology in a mouse model of gluten sensitivity, showing its potential as a solution for gluten related disorders (McCarville et al., 2017, Appl. Envoron. Microbiol. Vol. 83, no. 19, e01323-17).

SUMMARY OF THE INVENTION

The present inventors have surprisingly found that specific sugars can increase the expression of serpin when added to the growth medium of *B. longum* strain CNCM I-2618 (*B. longum* NCC 2705).

Accordingly, in a first aspect of the present invention, there is provided use of a sugar selected from lactose, fructose and raffinose, or combinations thereof for increasing serpin expression in *B. longum* strain CNCM I-2618.

In another aspect of the present invention, there is provided a method of increasing serpin expression in *B. longum* strain CNCM I-2618 wherein said method comprises growing *B. longum* strain CNCM I-2618 in a culture medium, characterised in that said culture medium comprises a sugar selected from lactose, fructose and raffinose, or combinations thereof.

According to another aspect of the present invention, there is provided *B. longum* strain CNCM I-2618 produced by a method of growing *B. longum* strain CNCM I-2618 in a culture medium, characterised in that said culture medium comprises a sugar selected from lactose, fructose and raffinose, or combinations thereof.

The *B. longum* strain CNCM I-2618 according to the present invention is associated with greater serpin production relative to a *B. longum* strain CNCM I-2618 grown in the absence of lactose, fructose or raffinose, or combinations thereof.

In one embodiment, the sugar is lactose.

According to the present invention, the *B. longum* strain CNCM I-2618 may be cultured in a medium comprising the sugar selected from lactose, fructose or raffinose, or combinations thereof at a concentration of, for example, 0.02 to 0.50 wt %.

For example, the *B. longum* strain CNCM I-2618 may be cultured in a medium comprising the sugar selected from lactose, fructose or raffinose, or combinations thereof at a concentration 0.05 to 0.15 wt %, 0.08 to 0.12 wt %, or about 0.10%.

According to another aspect of the present invention, there is provided a composition comprising the *B. longum* strain CNCM I-2618 produced according to the method described herein.

In one embodiment, the composition is a food, a medical food, a tube feed, or a nutritional supplement.

In one embodiment, the food is selected from milk, yoghurt, curd, cheese, fermented milks, milk based fermented products, rice based products, milk based powders, infant formulae and pet food.

In one embodiment, the composition is a pharmaceutical composition wherein the pharmaceutical composition comprises one or more pharmaceutically acceptable carriers, diluents and/or excipients.

According to another aspect of the present invention there is provided *B. longum* strain CNCM I-2618 produced according to the method described herein, or a composition comprising said *B. longum* strain CNCM I-2618, for use in the treatment or prevention of conditions related to gluten sensitivity or involving the reduced activity of serine protease inhibitors.

According to another aspect of the present invention there is provided *B. longum* strain CNCM I-2618 produced according to the method described herein, or a composition comprising said *B. longum* strain CNCM I-2618, for use in the treatment or prevention of a gluten-related disorder.

According to an aspect of the present invention there is provided *B. longum* strain CNCM I-2618 produced according to the method described herein, or a composition comprising said *B. longum* strain CNCM I-2618, for use in the treatment or prevention of, celiac disease, non-celiac gluten sensitivity, gluten ataxia, dermatitis herpetiformis or wheat allergy.

According to another aspect of the present invention there is provided *B. longum* strain CNCM I-2618 produced according to the method described herein, or a composition comprising said *B. longum* strain CNCM I-2618, for use in the treatment or prevention of inflammatory bowel disease.

It will also be appreciated that the sugar may also increase the production of serpin in *B. longum* strain CNCM I-2618 in vivo when the sugar is administered in combination with the *B. longum* strain CNCM I-2618.

Thus, according to another aspect of the present invention there is also provided a combination of (i) *B. longum* strain CNCM I-2618 and (ii) a sugar selected from lactose, fructose and raffinose, or combinations thereof.

According to another aspect of the present invention there is also provided a combination of (i) *B. longum* strain CNCM I-2618 and (ii) a sugar selected from lactose, fructose and raffinose, or a combination thereof, for use in the treatment or prevention of a condition related to gluten sensitivity or a condition linked to reduced levels of serine protease inhibitors.

In one embodiment, the combination is a combination of *B. longum* strain CNCM I-2618 and lactose.

According to another aspect of the present invention there is also provided *B. longum* strain CNCM I-2618 for use in the treatment or prevention of a condition related to gluten sensitivity or a condition linked to reduced levels of serine protease inhibitors, wherein the *B. longum* strain CNCM I-2618 is administered in combination with a sugar selected from lactose, fructose and raffinose, or a combination thereof.

According to another aspect of the present invention there is provided sugar selected from lactose, fructose and raffinose, or a combination thereof for use in the treatment or prevention of a condition related to gluten sensitivity, or a condition linked to reduced levels of serine protease inhibitors, wherein the sugar is administered in combination with *B. longum* strain CNCM I-2618.

DETAILED DESCRIPTION OF THE INVENTION

Composition

Figure 1:
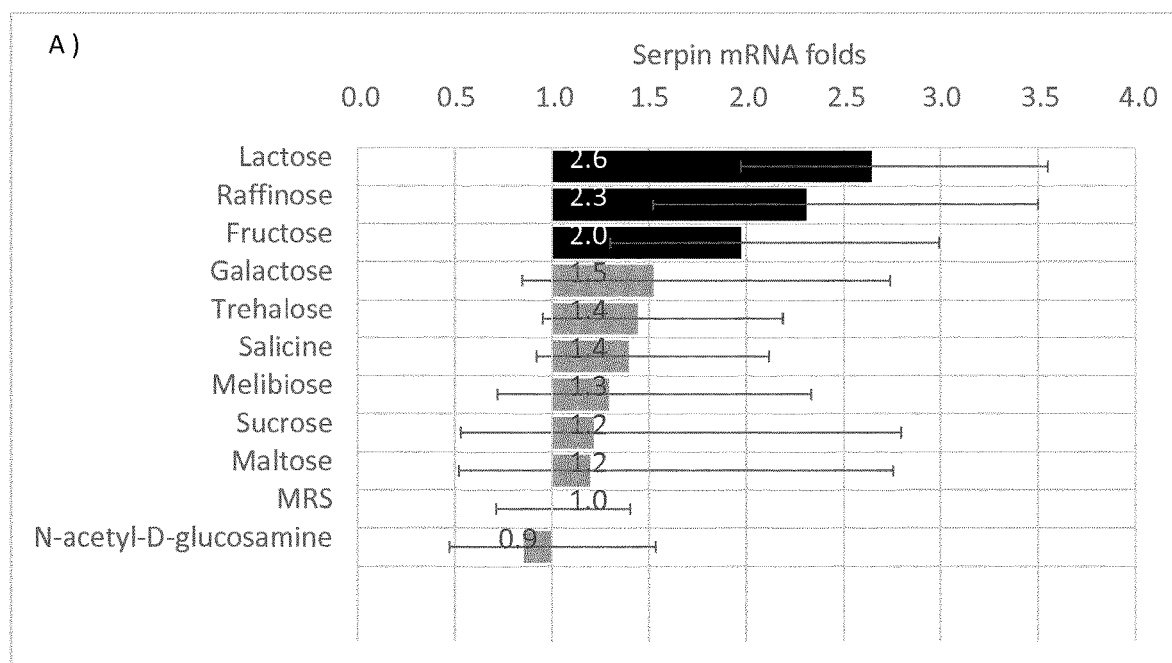
FIG. 1—Relative transcription level of serpin gene in *B. longum* NCC 2705 after 180 min sugar induction at a concentration of 0.1%. The bars indicate the relative amounts of serpin mRNAs for the specific samples comparing to that of growth in only MRSc. Black bars represent significant induction. The standard deviation was obtained from at least 2 different experiments (95% confidence interval).

The composition of the present invention may be in the form of a food, a medical food, a tube feed, a nutritional composition, or a nutritional supplement. The term "nutritional supplement" refers to a product which is intended to supplement the general diet of a subject.

In one embodiment, the food is selected from milk, yoghurt, curd, cheese, fermented milks, milk based fermented products, rice based products, milk based powders, infant formulae and pet food.

The composition may be in the form of a medical food. The term "medical food" as used herein refers to a food product specifically formulated for the dietary management of a medical disease or condition. The medical food may be administered under medical supervision. The medical food may be for oral ingestion or tube feeding.

The composition may be in the form of a tube feed. The term "tube feed" refers to a product which is intended for introducing nutrients directly into the gastrointestinal tract of a subject by a feeding tube. A tube feed may be administered by, for example, a feeding tube placed through the nose of a subject (such as nasogastric, nasoduodenal, and nasojejunal tubes), or a feeding tube placed directly into the abdomen of a subject (such as gastrostomy, gastrojejunostomy, or jejunostomy feeding tube).

The composition may in the form of a pharmaceutical composition and may comprise one or more suitable pharmaceutically acceptable carriers, diluents and/or excipients.

Examples of such suitable excipients for compositions described herein may be found in the "Handbook of Pharmaceutical Excipients", 2nd Edition, (1994), Edited by A Wade and P J Weller. Acceptable carriers or diluents for therapeutic use are well known in the pharmaceutical art, and are described, for example, in "Remington's Pharmaceutical Sciences", Mack Publishing Co. (A. R. Gennaro edit. 1985).

Examples of suitable carriers include lactose, starch, glucose, methyl cellulose, magnesium stearate, mannitol, sorbitol and the like. Examples of suitable diluents include ethanol, glycerol and water.

The choice of pharmaceutical carrier, excipient or diluent can be selected with regard to the intended route of administration and standard pharmaceutical practice. The pharmaceutical compositions may comprise as, or in addition to, the carrier, excipient or diluent any suitable binder(s), lubricant(s), suspending agent(s), coating agent(s) and/or solubilising agent(s).

Examples of suitable binders include starch, gelatin, natural sugars such as glucose, anhydrous lactose, free-flow lactose, beta-lactose, corn sweeteners, natural and synthetic gums, such as acacia, tragacanth or sodium alginate, carboxymethyl cellulose and polyethylene glycol.

Examples of suitable lubricants include sodium oleate, sodium stearate, magnesium stearate, sodium benzoate, sodium acetate, sodium chloride and the like.

Preservatives, stabilisers, dyes and even flavouring agents may be provided in the composition. Examples of preservatives include sodium benzoate, sorbic acid and esters of p-hydroxybenzoic acid. Antioxidants and suspending agents may be also used.

Nutritionally acceptable carriers, diluents and excipients include those suitable for human or animal consumption that are used as standard in the food industry. Typical nutritionally acceptable carriers, diluents and excipients will be familiar to the skilled person in the art.

The composition may be in the form of a tablet, dragee, lozenges, capsule, gel cap, powder, granule, solution, emulsion, suspension, coated particle, spray-dried particle or pill.

In an alternative embodiment the composition may be in the form of a composition for topical administration, such as a gel, cream, ointment, emulsion, suspension or solution for topical administration.

It is clear to those skilled in the art that an ideal dose will depend on the subject to be treated, its health condition, sex, age, or weight, for example, and the route of administration. The dose to be ideally used will consequently vary but can be determined easily by those of skill in the art.

However, generally, it is preferred if the composition of the present invention comprises between $10^6$ and $10^{10}$ cfu and/or between $10^6$ and $10^{10}$ cells of B. longum strain CM I-2618 per daily dose. It may also comprise between $10^6$ and $10^{11}$ cfu and/or between $10^6$ and $10^{11}$ cells of B. longum strain CM I-2618 per g of the dry weight of the composition.

Sugars

The sugars used in the present invention are selected from lactose, fructose and raffinose, or a combination thereof. Lactose is a disaccharide found in milk and composed of glucose and galactose. Fructose is a monosaccharide found in many plants. Raffinose is a trisaccharide also found in plants and composed of galactose, glucose and fructose.

The B. longum strain CNCM I-2618 may be cultured in a medium comprising lactose, fructose or raffinose, or a mixture thereof, at a concentration of, for example, 0.02 to 0.50 wt %. For example, the B. longum strain CNCM I-2618 may be cultured in a medium comprising lactose, fructose or raffinose, or mixtures thereof, at a concentration 0.05 to 0.15 wt %, 0.08 to 0.12 wt %, or about 0.10%.

The lactose, fructose, raffinose, or mixtures thereof, may be added to a conventional culture medium comprising up to 8 wt %, preferably up to 6 wt %, for example 4-6 wt %, of another sugar suitable to sustain B. longum growth, such as, but not limited to, glucose or sucrose. Conventional culture mediums suitable for growth of B. longum are well known to the person skilled in the art.

In one embodiment, the B. longum strain CNCM I-2618 may be cultured in a medium comprising the sugar at a concentration of 0.03 to 0.40, 0.04 to 0.30 or 0.05 to 0.20 wt %.

In one embodiment, the culture medium may comprise the lactose, fructose or raffinose, or a combination thereof, at a concentration of 0.03 to 0.15, 0.04 to 0.15, 0.05 to 0.15, 0.06 to 0.15 0.07 to 0.15, 0.08 to 0.15, 0.09 to 0.15 or 0.10 to 0.15 wt %.

In one embodiment, the culture medium may comprise the lactose, fructose or raffinose, or a combination thereof, at a concentration of 0.05 to 0.14, 0.05 to 0.13, 0.05 to 0.12 or 0.05 to 0.11 wt %.

In one embodiment, the culture medium may comprise the lactose, fructose or raffinose, or a combination thereof, at a concentration of 0.06 to 0.14, 0.07 to 0.13, 0.08 to 0.12, 0.09 to 0.11 or about 0.10 wt %.

In one embodiment, lactose is used at the concentrations described above.

In one embodiment, fructose is used at the concentrations described above.

In one embodiment, raffinose is used at the concentrations described above.

Process for Producing a Culture Powder

Strains belonging to the species B. longum are grown in anaerobic conditions. Fermentation methods under anaerobic conditions are commonly known. The skilled person is able to identify suitable components of the fermentation medium and to adjust fermentation conditions based on his general knowledge, depending on the microorganism to be grown. The fermentation medium typically comprises
- a nitrogen source such as yeast extract,
- a carbon source such as a sugar,
- various growth factors (e.g minerals, vitamins etc.) required by the microorganism and
- water.

A non-limiting example of a typical growth medium for B. longum is MRS (De Man, Rogosa and Sharpe) medium, supplemented with 0.05% of cysteine (MRSc).

The fermentation is preferably carried out in two steps, a starter fermentation being carried out prior to the main fermentation step. The fermentation medium can be different for the starter and the main fermentation or may be identical.

The second step of the process is the concentration of the biomass. This can also be carried out using methods known to the person skilled in the art, such as for example centrifugation or filtration. The total solid content of the biomass after concentration is preferably comprised between 10 and 35 wt %, preferably between 14 and 35 wt %, based on the total dry weight of the biomass (i.e. of the total amount of fermentation medium and produced microorganism).

Optionally, the concentration may be preceded or combined with a washing step to remove residues of the fermentation medium and/or compounds produced during fermentation. For example, washing may be performed by concentrating biomass, re-suspending the concentrated biomass in a buffer, such as a phosphate buffer, or a similar composition and re-concentrating the biomass.

For example, the process described in WO2017/001590, which is entirely incorporated by reference, can be applied.

Combination

In one aspect of the present invention, there is provided a combination of (i) B. longum strain CNCM I-2618 and (ii) a sugar selected from lactose, fructose and raffinose.

As used herein, the term "combination" refers to the combined administration of B. longum strain CNCM I-2618 and lactose, fructose or raffinose, wherein the B. longum strain CNCM I-2618 and the sugar may be administered simultaneously or sequentially.

As used herein, the term "simultaneous" or "simultaneously" is used to mean that the two agents (B. longum strain CNCM I-2618 and the sugar) are administered concurrently, i.e. at the same time.

The term "sequential" or "sequentially" is used to mean that the two agents are administered one after the other, where either the B. longum strain CNCM I-2618 or the sugar may be administered first.

The agents may be administered either as separate formulations or as a single combined formulation.

When the compounds are co-formulated, i.e. in the same composition or formulation, they can only be administered simultaneously. When the compounds are formulated in separate compositions or formulations, they can be administered simultaneously or sequentially. Simultaneous administration of the agents in the same formulation or in separate formulations can also be described as the co- or joint administration of the two compounds.

In one embodiment, B. longum strain CNCM I-2618 and the sugar are in admixture. In another embodiment, the B. longum strain CNCM I-2618 and sugar are present in the form of a kit comprising a preparation of the two agents and, optionally, instructions for the simultaneous or sequential administration of the preparations to a subject in need thereof.

Treatment

The B. longum strain CNCM I-2618 produced according to the present invention, or a composition comprising the same, may be for use in the treatment or prevention of gluten-related disorders or conditions involving a reduced activity of serine protease inhibitors.

For example the B. longum strain CNCM I-2618 produced according to the present invention, or a composition comprising the same, may be for use in the treatment or prevention of inflammatory bowel disease, celiac disease, non-celiac gluten sensitivity, gluten ataxia, dermatitis herpetiformis and wheat allergy.

Preferably the disease is a gluten-related disorder. Gluten-related disorders encompass diseases triggered by gluten. The terms "conditions related to gluten sensitivity" and "gluten-related disorders" are used interchangeably herein.

Gluten-related disorders include celiac disease, non-celiac gluten sensitivity, gluten ataxia, dermatitis herpetiformis and wheat allergy.

Celiac Disease

Celiac disease is one of the most common immune mediated disorders. It is a worldwide condition and is prevalent especially in the United States and Europe where around 1% of subjects had positive antibody tests. Celiac disease is a complex disorder which arises from a complicated interaction among various immunologic, genetic, and environmental factors. It is triggered by the digestion of wheat gluten and other related cereal proteins such as rye and barley proteins. Symptoms linked with celiac disease are growth retardation, irritability and pubertal delay in children and many gastrointestinal symptoms like discomfort, diarrhoea, occult stool, steatorrhea flatulence.

Clinical evidence shows class II human leukocyte antigens (HLA-DQII), which strongly relate with celiac disease pathology, are expressed in about 95% of celiac disease patients. In the intestinal lumen, gluten protein are partially digested, forming proteolytic-resistant 33-mer gluten peptide. After crossing the small intestinal barrier, they are deamidated by transglutaminase 2 (TG2) with negative charges (Sollid, 2000, Annual review of immunology, 18(1), 53-81), which then bind to the positively charged binding sites of HLA-DQ2.5/8 (Dieterich et al., 1997, Nature medicine, 3(7), 797-801). HLA-DQ2.5/8 displaying those specific gluten peptides signals to helper T cells and other immune cells causing further damage in the small intestine. Antibodies against gluten proteins and autoantibodies to connective tissue components (TG2) are also associated with celiac disease progression (Alaedini & Green, 2005, Annals of internal medicine, 142(4), 289-298).

Non-Celiac Gluten Sensitivity

Non-celiac gluten sensitivity (also designated as non-celiac wheat sensitivity) is an emerging condition. It is defined as a clinical entity induced by the ingestion of gluten leading to intestinal and/or extraintestinal symptoms which could be improved by removing the gluten-containing foodstuff from the diet (Lundin & Alaedini, 2012). The pathogenesis of non-celiac gluten sensitivity is not yet well understood. It has been shown that except for gliadin (main cytotoxic antigen of gluten), other proteins/peptides present in gluten and gluten-containing cereals (wheat, rye, barley, and their derivatives) may play a role in the development of symptoms. Non-celiac gluten sensitivity is the most common syndrome of gluten-related disorders with prevalence rates between 0.5-13% in the general population (Catassi et al., 2013, Nutrients, 5(10), 3839-385). The diagnosis of non-celiac gluten sensitivity is made by exclusion of other gluten-related disorders.

Dermatitis Herpetiformis

Dermatitis herpetiformis is a chronic blistering skin autoimmune condition, characterized by the presence of skin lesions that have an extensive and symmetrical distribution, predominating in areas of greater friction, and affecting mainly both elbows, knees, buttocks, ankles, and may also affect the scalp and other parts of the body. The lesions are vesicular-crusted and when they flake off, they evolve to pigmented areas or a chromic and intense burning, itchy and blistering rash.

The age of onset is variable. It may start in children and adolescents but can also affect individuals of both sexes indistinctly at any age of their lives.

People with dermatitis herpetiformis have different degrees of intestinal involvement, ranging from milder mucosal lesions to the presence of villous atrophy.

Wheat Allergy

Gastrointestinal symptoms of wheat allergy are similar to those of celiac disease and non-celiac gluten sensitivity, but there is a different interval between exposure to wheat and onset of symptoms. Wheat allergy has a fast onset (from minutes to hours) after the consumption of food containing wheat and can lead to anaphylaxis.

Gluten Ataxia

Gluten ataxia is a gluten-related disorder. With gluten ataxia, damage takes place in the cerebellum, the balance center of the brain that controls coordination and complex movements like walking, speaking and swallowing. Gluten ataxia is the single most common cause of sporadic idiopathic ataxia. It accounts for 40% of ataxias of unknown origin and 15% of all ataxias.

Gluten ataxia is an immune-mediated disease triggered by the ingestion of gluten in genetically susceptible individuals. It should be considered in the differential diagnosis of all patients with idiopathic sporadic ataxia. The effectiveness of the treatment depends on the elapsed time from the onset of the ataxia until diagnosis. The death of neurons in the cerebellum as a result of gluten exposure of the subject is irreversible.

Early diagnosis and treatment with a gluten free diet can improve ataxia and prevent its progression. Less than 10% of people with gluten ataxia present any gastrointestinal symptom, yet about 40% have intestinal damage. Sensitive markers of gluten ataxia include anti-gliadin antibodies. Immunoglobulin A (IgA) deposits against transglutaminase 2 (TG2) in the small bowel and at extraintestinal sites are proving to be additionally reliable.

Administration

The *B. longum* strain CNCM I-2618 or composition described herein are preferably administered enterally.

Enteral administration may be oral, gastric, and/or rectal.

In general terms, administration of the combination or composition described herein may, for example, be by an oral route or another route into the gastro-intestinal tract, for example the administration may be by tube feeding.

In an alternative embodiment administration of the combination or composition described herein may be topical administration.

The subject may be a mammal such as a human, canine, feline, equine, caprine, bovine, ovine, porcine, cervine and primates. Preferably the subject is a human.

Preferred features and embodiments of the invention will now be described by way of non-limiting examples.

The practice of the present invention will employ, unless otherwise indicated, conventional techniques of chemistry, biochemistry, molecular biology, microbiology and immunology, which are within the capabilities of a person of ordinary skill in the art. Such techniques are explained in the literature. See, for example, Sambrook, J., Fritsch, E. F. and Maniatis, T. (1989) Molecular Cloning: A Laboratory Manual, 2nd Edition, Cold Spring Harbor Laboratory Press; Ausubel, F. M. et al. (1995 and periodic supplements) Current Protocols in Molecular Biology, Ch. 9, 13 and 16, John Wiley & Sons; Roe, B., Crabtree, J. and Kahn, A. (1996) DNA Isolation and Sequencing: Essential Techniques, John Wiley & Sons; Polak, J. M. and McGee, J. O'D. (1990) In Situ Hybridization: Principles and Practice, Oxford University Press; Gait, M. J. (1984) Oligonucleotide Synthesis: A Practical Approach, IRL Press; and Lilley, D. M. and Dahlberg, J. E. (1992) Methods in Enzymology: DNA Structures Part A: Synthesis and Physical Analysis of DNA, Academic Press. Each of these general texts is herein incorporated by reference.

EXAMPLES

Example 1—Methods

BL NCC 2705 (*B. longum* strain CNCM I-2618) was grown in Biolector (growth conditions—anaerobic, 37° C., MRS+5 mM L-cysteine (MRSc).

48-well microtiter plate with pH sensor and dissolved oxygen (DO) sensor were used to culture the strains in Biolector (m2p-labs Aachen, Germany). It was continuously shaken to prevent bacteria aggregation and measurements were performed every 15 min. Plates were sealed with a gas permeable film and an anaerobe-chamber provides well-defined anaerobic gassing conditions. Fermentation parameters like biomass, pH and dissolved oxygen (DO) were monitored online throughout the entire growth using the BioLection HMI software. Growth parameters were:

Inoculation rate (%) 2
Volume for each wall (ml) 1
Fermentation time (h) 16
Temperature (° C.) 37
External gas supplied $N^2$
External gas pressure (bar) 2
Shaking frequency (rpm) 400
Measurement cycle time (min) 15

The following carbohydrates were added to the cultures individually:

Monosaccharides—Glucose, N-Acetyl-glucosamine, Fructose, Galactose.
Disaccharides—Lactose, Melibiose, Sucrose
Polysaccharides—Raffinose, All sugars were purchased from Sigma-Aldrich.

*B. longum* NCC 2705 was then further cultivated in the same conditions for 180 min, after which samples (500 µl) were collected and serpin mRNA levels measured. Every fermentation was performed at least in duplicate.

As shown in FIG. 1, lactose, fructose and raffinose were shown to increase serpin mRNA levels of *B. longum* NCC 2705.

Serpin mRNA Detection and Quantification

Total RNA isolation—500 µl of bacterial cultures were suspended in 1 ml of RNA protect bacteria reagent (Qiagen, Germany) and briefly centrifuged 10 min at 5000 g to harvest cells for total RNA extraction.

Total RNA was extracted using the RNeasy total RNA Mini kit (Qiagen, Germany, Ca. No. 74101) with protease K (Qiagen, Germany, Ca. No. 19131) and further treated using RNase-free DNase set (Qiagen, Germany, Ca. No. 79254). Total RNA was then eluted in 40 µl water.

RNA quality control and quantification—Quality and quantity control of RNA samples were analysed by electrophoresis using QIAxcel Advanced System (Qiagen, Germany).

1 µl of RNA samples and RNA size marker were mixed separately with the same volume of RNA Denaturation Buffer and incubated 2 min at 70° C., followed by 1 min cooling on ice. Then samples were diluted by QX RNA Dilution to 10 µl for analysing and measurement. Evaluation of RNA quality was performed using the ratio of 23S over 16S. RNA with a ratio value between 1.6 to 2.3 were selected for later qRT-PCR.

Both cDNA synthesis and PCR were performed in a one-step reaction, using the ABI Prism 7900HT system with the SuperScript III Platinum SYBR Green One-Step qRT-PCR Kit with ROX (Invitrogen, cat. No. 11746-500).

PCR products were detected with SYBR green fluorescent dye and normalized with ROX reference dye.

The following primers were used for cDNA synthesis: for serpin gene: forward 5'-ACCAATCGCTGCTAAGTTCG-3', reverse 5'-TCGCTGGCAAGAGAGTAGTC-3'; for ldh: forward, 5'-CGAACGCCATCTACATGCTC-3' and reverse, 5'-AAGATCTGGTTCTCTTGCAG-3'. The primers for serpin were created based on *B. longum* NCC 2705 and DNA homology was checked in *B. longum* ATCC15707. The reliability was verified by dissociation curve analysis.

mRNA fold expression analysis method—The Pfaffl method was used to calculate relative transcription changes (Pfaffl, 2012, Martin Filion, Hg., Quantitative real-time PCR in Applied Microbiology, 53-62) for which the equation is shown in Equation 1:

$$\text{Relative Quantity} = \frac{E_{ref\ target}^{CT_{ref\ target}}}{E_{ref\ calibrator}^{CT_{ref\ calibrator}}} \div \frac{E_{sample\ target}^{CT_{sample\ target}}}{E_{sample\ calibrator}^{CT_{sample\ calibrator}}} \quad \text{Equation 1}$$

Example 2—Results

In order to optimize the effect of lactose on induction of BL NCC 2705 serpin, a dose response was performed. The fermentation was performed in a 10 L Biostar B Plus fermenter with MRSc medium, supplemented with 0.05% cysteine as base, and different concentration of lactose (0.05%, 0.1%, 1%, 2% and 2.75%) were added to the medium. Glucose was supplemented to the different recipes to reach a final total amount of 5.5% of total sugar. Serpin mRNA fold induction was calculated using the 8 h MRSc grown BL NCC 2705 culture as a base (FIG. 2).

Figure 2:
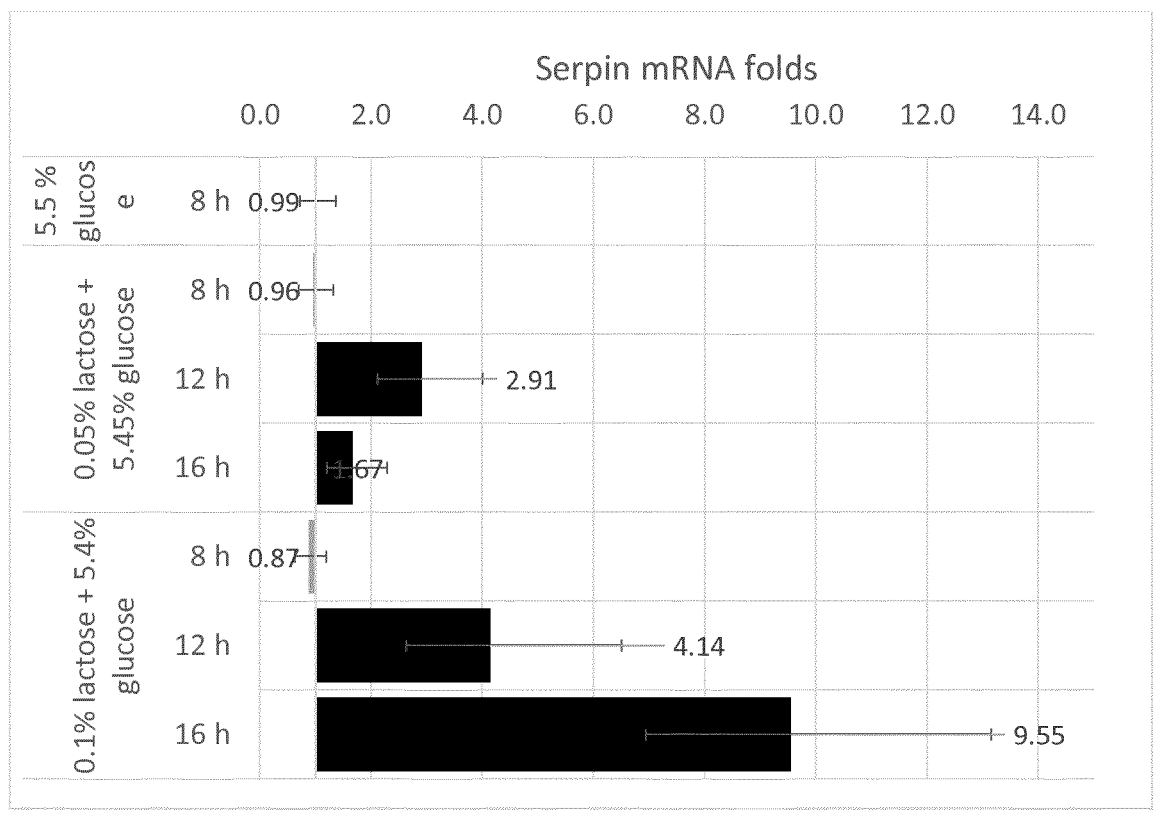
FIG. 2—Serpin mRNA level of *B. longum* NCC 2705 fermented in different growth medium after 8 h, 12 h and 16 h. Different proportions of glucose was replaced by lactose and fructose as shown in the y-axis and the total amount of sugar percentage was kept stable at 5.5%. The values were calculated based on *B. longum* NCC 2705 growth after 8 h in 5.5% glucose. Black bars represent significant induction.

As depicted in FIG. 2, the highest serpin mRNA level at end of fermentation (16 h) reached by using lactose was observed with the addition of 0.1%).

The invention claimed is:

1. A method for treatment of inflammatory bowel disease, celiac disease, non-celiac gluten sensitivity, gluten ataxia, dermatitis herpetiformis or wheat allergy in a subject in need thereof, the method comprising administering to the subject a composition comprising *B. longum* strain CNCM I-2618 and 0.03 to 0.40 wt % of a sugar selected from the group consisting of lactose, fructose, raffinose, and combinations thereof.

2. The method of claim 1, wherein the *B. Longum* strain CNCM I-2618 and the sugar are administered simultaneously or sequentially.

3. The method of claim 1, wherein the *B. Longum* strain CNCM I-2618 and the sugar are coformulated.

4. The method of claim 1, wherein the *B. Longum* strain CNCM I-2618 and the sugar are provided in separate compositions.

5. The method of claim 1, wherein the composition is adminstered enterally.

6. The method of claim 1, wherein the subject is selected from the group consisting of human, canine, feline, equine, caprine, bovine, ovine, porcine, cervine, and primate.

7. The method of claim 1, wherein the *B. Longum* strain CNM I-2618 is produced by growing the *B. Longum* strain CNM I-2618 in a culture medium comprising the sugar.

8. The method of claim 7, wherein the culture medium comprises the sugar at a concentration of 0.02 to 0.5 wt %.

9. The method of claim 7, wherein the culture medium comprises the sugar at a concentration of 0.05 to 0.15 wt %.

10. The method of claim 7, wherin the the sugar in the culture medium comprises lactose.

11. The method of claim 1, wherein the sugar comprises lactose.

12. The method of claim 1, wherein the composition comprises 0.04 to 0.30 wt % of the sugar.

13. The method of claim 1, wherein the composition comprises 0.05 to 0.20 wt % of the sugar.

14. The method of claim 7, wherein the culture medium comprises 0.04 to 0.30 wt % of the sugar.

15. The method of claim 7, wherein the culture medium comprises 0.05 to 0.20 wt % of the sugar.

* * * * *